United States Patent [19]

Takagaki et al.

[11] Patent Number: 5,981,495
[45] Date of Patent: Nov. 9, 1999

[54] BENZOPYRAN DERIVATIVE AND METHOD FOR TREATING HEART DISEASE USING THIS DERIVATIVE

[75] Inventors: Hidetsugu Takagaki; Nobuyuki Kimura, both of Sakura; Yasuo Aoki, Yotsukaido; Shigenori Nakanishi, Sakura; Masayoshi Abe, Chiba; Osamu Misumi, Sakura, all of Japan

[73] Assignee: Dainippon Ink and Chemicals, Inc., Tokyo, Japan

[21] Appl. No.: 08/821,569

[22] Filed: Mar. 19, 1997

[30] Foreign Application Priority Data

Mar. 22, 1996 [JP] Japan ................. 8-066102
Jan. 14, 1997 [JP] Japan ................. 9-004575

[51] Int. Cl.$^6$ .......... A61K 31/70; A61K 31/37; A61K 31/35; C07D 311/08
[52] U.S. Cl. .......... 514/25; 514/455; 514/457; 549/282; 549/285; 536/8
[58] Field of Search .......... 514/25, 455, 457; 549/282, 285; 536/8

[56] References Cited

U.S. PATENT DOCUMENTS

| | | | |
|---|---|---|---|
| 4,845,121 | 7/1989 | Witiak et al. | 514/455 |
| 4,971,982 | 11/1990 | Attwood et al. | 514/337 |
| 5,428,059 | 6/1995 | Takagaki et al. | 514/457 |
| 5,580,552 | 12/1996 | Takagaki et al. | 536/18.1 |

FOREIGN PATENT DOCUMENTS 0 598 117  5/1994  European Pat. Off. .
0 684 255  11/1995  European Pat. Off. .
9213852  8/1992  WIPO .

OTHER PUBLICATIONS

Witiak et al., Synthetic Aci–Reductones: 3,4–Dihydroxy2–H–I–benzopyran–2–ones and Their cis–and trans–4a,5,6,7,8,8a–Hexahydro Diastereomers. Antiaggregatory, Antilipidemic, and Redox Properties Compared to Those of the 4–Substituted 2–Hydroxytetronic Acids, J. Med. Chem. 1988, vol. 31, pp. 1437–1445.

*Primary Examiner*—Gary L. Kunz
*Assistant Examiner*—Everett White
*Attorney, Agent, or Firm*—Armstrong, Westerman, Hattori, McLeland & Naughton

[57] ABSTRACT

The present invention offers a safe and effective drug for heart diseases and a safe and effective method for treating heart diseases such as ischemic heart disease and cardiac arrhythmia. The method comprises administering a pathologically effective amount of a benzopyran derivative expressed by the following general formula (I):

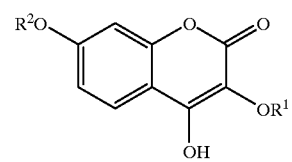

wherein $R^1$ is an alkyl group or an alkenyl group, $R^2$ is a hydrogen atom, an alkyl group, an alkyl group having at least one hydroxyl group, an alkenyl group, an acyl group or a glycosyl group; or physiologically acceptable salts thereof.

21 Claims, No Drawings

BENZOPYRAN DERIVATIVE AND METHOD FOR TREATING HEART DISEASE USING THIS DERIVATIVE

BACKGROUND OF THE INVENTION

1. Technical Field of the Invention

The present invention relates to drugs and methods for treating heart disease using benzopyran derivatives and salts thereof.

2. Background Art

The present inventors have previously reported on the anti-allergy effect of benzopyran derivatives in International Patent Publication No. WO 92/13852, Japanese Patent Application, First Publication No. Hei 8-198890 and U.S. Pat. No. 5,428,059, the disclosure of which is incorporated herein by reference.

Compounds corresponding to the benzopyran derivatives of the present invention have been described in U.S. Pat. No. 4,845,121 and Donald T. Witiak, *J. Med. Chem.*, vol. 31, p. 1437–1445, 1988. However, these benzopyran derivatives and physiologically acceptable salts thereof have conventionally not been known to be effective in treating heart disease.

Additionally, benzopyran derivatives wherein the 7-position substituent group is an alkyl group having at least one hydroxyl group and physiologically acceptable salts thereof are compounds which the present inventors have newly synthesized as a result of synthesizing numerous types of benzopyran derivatives and analyzing them for the purposes of offering an effective method of treating heart disease, and their pharmacological effects have been conventionally unknown.

Although numerous pharmaceuticals for treating ischemic heart disease and arrhythmia have been available on the market, they are prone to having severe side effects, especially the medications for treating arrhythmia for which the difference between an effective dose and a toxic dose is small, thus making their therapeutic use difficult.

SUMMARY OF THE INVENTION

The object of the present invention is to offer a drug and a method for treating heart disease using benzopyran derivatives as treatment agents which are low in toxicity and have excellent therapeutic effects with respect to heart diseases such as ischemic heart disease and cardiac arrhythmia.

In order to offer an effective drug and method for treating heart diseases such as ischemic heart disease and cardiac arrhythmia, the present inventors synthesized numerous types of benzopyrans described in International Patent Publication No. WO 92/13852, Japanese Patent Application, First Publication No. Hei 8-198890 and U.S. Pat. No. 5,428,059 as well as new benzopyran derivatives, and evaluated these for their effectiveness in treating heart disease and safety, whereupon they discovered that the benzopyran derivatives shown by general formula (I) are extremely effective in treating heart disease and have low toxicity.

The present invention offers a drug for heart disease having as an active ingredient a pathologically effective amount of a benzopyran derivative expressed by the following general formula (I):

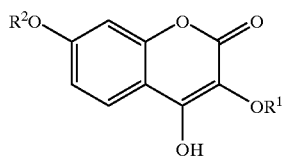

wherein $R^1$ is an alkyl group or an alkenyl group, $R^2$ is a hydrogen atom, an alkyl group, an alkyl group having a hydroxyl group, an alkenyl group, an acyl group or a glycosyl group; or physiologically acceptable salts thereof.

The present invention also offers a method for treating heart disease comprising administering a pathologically effective amount of a benzopyran derivative expressed by the following general formula (I):

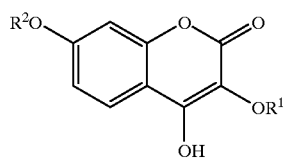

wherein $R^1$ is an alkyl group or an alkenyl group, $R^2$ is a hydrogen atom, an alkyl group, an alkyl group having a hydroxyl group, an alkenyl group, an acyl group or a glycosyl group; or physiologically acceptable salts thereof.

Additionally, the present invention offers a benzopyran derivative expressed by the following general formula (II):

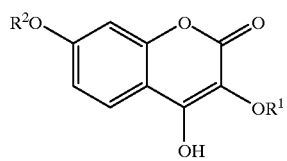

wherein $R^1$ is an alkyl group having 1–10 carbon atoms or an alkenyl group having 2–10 carbon atoms, and $R^2$ is an alkyl group having 2–4 carbon atoms and a hydroxyl group.

PREFERRED EMBODIMENTS OF THE INVENTION

General Formula (I)

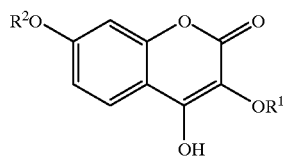

The benzopyran derivatives used for the present invention are expressed by the general formula (I), wherein $R^1$ is an alkyl group or an alkenyl group. If the alkyl group is a non-cyclic alkyl group, the alkyl group can be either a straight-chain or branched alkyl group, preferably an alkyl group having 1–10 carbon atoms, more preferably 2–8 carbon atoms.

Examples of such alkyl groups are methyl group, ethyl group, propyl group, isopropyl group, n-butyl group, s-butyl group, t-butyl group, n-pentyl group, n-hexyl group, 2-methylpentyl group, n-heptyl group, 1-ethylpentyl group, 4-methylpentyl group, 1-ethylbutyl group, n-octyl group, 1-ethylhexyl group, n-decyl group and n-dodecyl group.

Examples of alkenyl groups are straight-chain or branched alkenyl groups, preferably alkenyl groups having 2–10 carbon atoms, more preferably 4–8 carbon atoms. More specific examples are vinyl group, propenyl group, pentenyl group, hexenyl group, heptenyl group, octenyl group, nonyl group, decenyl group, 3-methyl-2-butenyl group, and geranyl group.

In general formula (I), $R^2$ is a hydrogen atom, an alkyl group, an alkyl group having at least one hydroxyl group, an alkenyl group, an acyl group or a glycosyl group.

In this case, the alkyl group may be either a straight-chain or branched alkyl group, preferably an alkyl group having 1–10 carbon atoms, more preferably 1–4 carbon atoms.

More specific examples are methyl group, ethyl group, propyl group, isopropyl group, n-butyl group, s-butyl group, t-butyl group, n-pentyl group, 2-methylpentyl group, n-hexyl group, n-octyl group, n-decyl group and n-dodecyl group.

The alkyl group having hydroxyl group is an alkyl group having at least one hydroxyl group, preferably an alkyl group having 1 or 2 hydroxyl groups and 2–4 carbon atoms. More specific examples are 2-hydroxyethyl group, 3-hydroxypropyl group, 4-hydroxybutyl group, 2,3-dihydroxypropyl group and 3,4-dihydroxybutyl group.

Additionally, compounds having substituent groups with protected hydroxyl groups are included as alkyl groups having hydroxyl groups according to the present invention. Examples of protective groups for hydroxyl groups are acetyl groups, propionyl groups and benzoyl groups, and an example of protective groups of adjacent hydroxyl groups is isopropylidene group.

Examples of alkenyl groups are straight-chain or branched alkenyl groups, preferably alkenyl groups having 2–10 carbon atoms, more preferably 2–4 carbon atoms. More specific examples are vinyl group, propenyl group, pentenyl group, hexenyl group, heptenyl group, octenyl group, nonyl group, decenyl group, 3-methyl-2-butenyl group and geranyl group.

The acyl group should preferably be an alkanoyl group having 1–10 carbon atoms. Specific examples are alkanoyl groups such as acetyl group, propionyl group, butyryl group and isobutyryl group; aroyl groups such as benzoyl group and benzoyl group having substituent groups including p-methoxybenzoyl group, p-methylbenzoyl group, p-chlorobenzoyl group and p-nitrobenzoyl group; and alkoxycarbonyl groups such as methoxycarbonyl group and ethoxycarbonyl group.

Examples of glycosyl groups are glucosyl group, mannosyl group and galactosyl group, of which all or a portion of the hydroxyl groups which do not contribute to the bond of the glycosyl group may be protected by protective groups, but unprotected glycosyl groups are more preferable. D-configuration and L-configuration stereoisomers of these are also included in this invention.

These 7-glycosiloxybenzopyran derivatives are compounds having a hexose derivative glycoside-bonded to the 7th position of a benzopyran derivative. While glycoside bonds may be of either an a-bond type or b-bond type bond format, the compounds of the present invention include both bond formats.

With regard to the glycosyl groups protected by protective groups, those which are generally used as protective groups for sugars can be given as examples of types of protective groups. For example, acyl groups and arallyl groups are suitable.

Examples of acyl groups are alkanoyl groups such as acetyl group, propionyl group, butyryl group and isobutyryl group; aroyl groups such as benzoyl group and benzoyl group having substituent groups including p-methoxybenzoyl group, p-methylbenzoyl group, p-chlorobenzoyl group and p-nitrobenzoyl group; and alkoxycarbonyl groups such as methoxycarbonyl group and ethoxycarbonyl group. Preferably, they are alkanoyl groups.

Examples of aralkyl groups are benzyl group and benzyl group having substituent groups, such as p-methoxybenzyl group, p-methylbenzyl group, p-chlorobenzyl group and p-nitrobenzyl group. The protective groups are preferably be benzyl group or acetyl group. More preferably, the protective groups are acetyl groups.

While the preferable glycosyl group changes according to the substituent group of $R^1$, the order of preference is glucose, galactose and mannose. Compounds which are preferable in terms of heart disease treatment are compounds expressed by general formula (I) wherein $R^1$ is an alkyl group and $R^2$ is a hydrogen atom, wherein $R^1$ is an alkyl group and $R^2$ is a glucosyl group, wherein $R^1$ is an alkenyl group and $R^2$ is a hydrogen atom, wherein $R^1$ is an alkyl group and $R^2$ is a 2-hydroxyethyl group, wherein $R^1$ is an alkyl group and $R^2$ is a glyceroxy group, or wherein $R^1$ and $R^2$ are alkyl groups.

Next, the method for producing benzopyran derivatives according to the present invention is explained in brief. The production method for the benzopyran derivative expressed by the general formula (I) according to the present invention can be performed by the following reaction path using the method disclosed in U.S. Pat. No. 5,428,059.

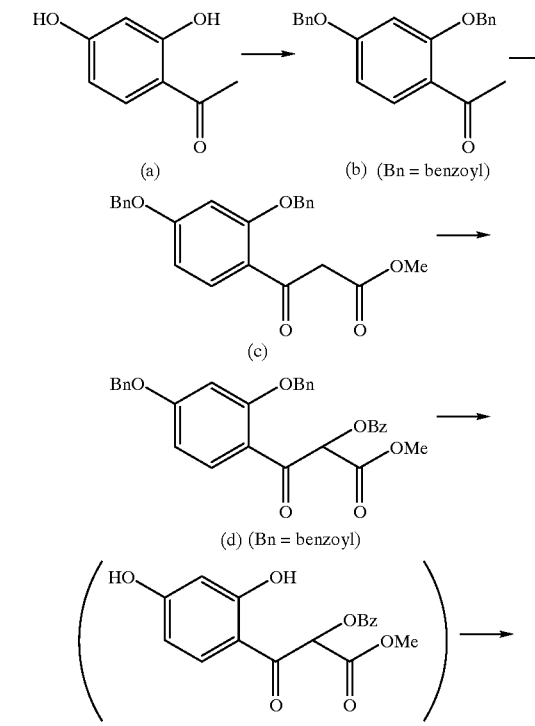

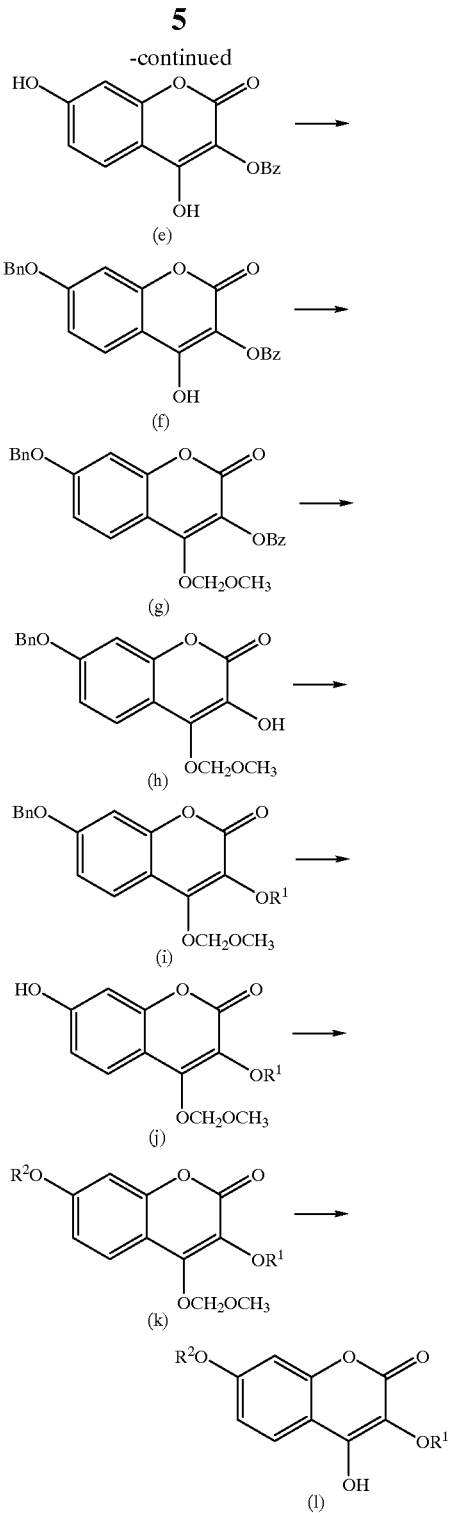

which a methoxymethyl group is added to the 4-position to form (g). After removing the benzoyl group from compound (g), an alkyl group ($R^1$) is added to the 3-position to form (i), after which the protective group is removed from the 7-position (j).

If $R^2$ is an alkyl group, an alkenyl group, an acyl group or a glycosyl group, the 7-position hydroxyl of compound (j) is alkylated, alkenylated, acylated, or glycosylated by means of a hexose derivative protecting the hydroxyl groups to form the compound (k), then the hydroxyl group in the 4-position is removed to result in the objective compound (l).

If $R^2$ is an alkyl group having hydroxyl group, an alkylation reaction is induced between the 7-position hydroxyl group of compound (j) and an alkyl group with the hydroxyl protected, then the protective group is removed. As an example, the case wherein the 7-position hydroxyl group is substituted with a 2-hydroxyethyl group is explained in detail below.

First, an alkylation reaction is performed between compound (j) and 2-acetoxyethyl bromide in the presence of a basic compound. As examples of basic compounds which can be used in this case, there are inorganic salts such as sodium bicarbonate, sodium carbonate, potassium bicarbonate, potassium carbonate, sodium hydroxide and potassium hydroxide; metal alcoholates such as sodium methoxide, sodium ethoxide, sodium t-butoxide and potassium t-butoxide; and metallic hydrides such as sodium hydride and potassium hydride.

The reaction is conducted in an organic solvent. Examples of organic solvents which can be used are hydrocarbons such as benzene, toluene and xylene; ethers such as diethyl ether, tetrahydrofuran and 1,2-dimethoxyethane; and amides such as N,N-dimethylformamide, N,N-dimethylacetoamide and 1-methyl-2-pyrrolidone. The reaction temperature is 0~100° C., preferable 20~50° C., and the reaction time is normally 1~5 hours.

Next, if necessary, the acetyl group which is a protective group is removed, and this reaction can be a de-acetylation reaction conducted under ordinary alkaline conditions. In this way, the objective 2-hydroxyethyl compound can be produced.

Furthermore, a compound substituted with an alkyl group having adjacent hydroxyl groups can be produced by conducting an alkylation reaction with an alkyl group having a hydroxyl group protected preferably by an isopropylidene group. In this case, the alkylation reaction can be performed by the same method as described above, and the de-protection reaction after the alkylation reaction can be performed by a ordinary isopropylidene de-protection method.

For example, the objective compound substituted with an alkyl group having a hydroxyl group can be produced by performing the reaction in an acetic acid solution or in a mixture of hydrochloric acid and dioxane, either at room temperature or while heating. If $R^2$ is a hydroxyl group, the objective compound (l) can be produced by de-protecting the 4-position and the 7-position of compound (i). If $R^1$ is an alkenyl group, an alkenyl group can be added by a conventional method instead of adding an alkyl group to the 3-position by the above method.

The following compounds are illustrative examples of benzopyran derivatives of the present invention.

3,7-dimethoxy-4-hydroxy-2H-1-benzopyran-2-one (compound 1), 3-methoxy-4-hydroxy-7-propoxy-2H-1-benzopyran-2-one (compound 2), 3-methoxy-4-hydroxy-7-hexyloxy-2H-1-benzopyran-2-one (compound 3), 3-ethoxy- First, the hydroxyl group of the 2,4-dihydroxyacetophenon (a) is protected by a benzyl group to result in (b). Next, a condensation reaction is conducted with dimethyl carbonate to form a ketoester (c), which is then reacted with benzoyl peroxide to form (d). The benzyl group which is the protective group of the hydroxyl is removed by means of a hydrogenation, and a treatment with acid results in the benzoyloxy compound (e).

Subsequently, the 7-position of this benzoyloxy compound (e) is protected by a benzyl group to form (f), after 4-hydroxy-7-methoxy-2H-1-benzopyran-2-one (compound 4), 3,7-diethoxy-4-hydroxy-2H-1-benzopyran-2-one (compound 5), 3-ethoxy-4-hydroxy-7-hexyloxy-2H-1-benzopyran-2-one (compound 6), 3-butoxy-4-hydroxy-7-methoxy-2H-1-benzopyran-2-one (compound 7), 3-butoxy-4-hydroxy-7-ethoxy-2H-1-benzopyran-2-one (compound 8), 3-butoxy-4-hydroxy-7-hexyloxy-2H-1-benzopyran-2-one (compound 9), 3-hexyloxy-4-hydroxy-7-methoxy-2H-1-benzopyran-2-one (compound 10), 3-hexyloxy-4-hydroxy-7-propoxy-2H-1-benzopyran-2-one (compound 11), 3-octyloxy-4-hydroxy-7-ethoxy-2H-1-benzopyran-2-one (compound 12), 3-decyloxy-4-hydroxy-7-methoxy-2H-1-benzopyran-2-one (compound 13), 3-(1-butenyloxy)-4-hydroxy-7-methoxy-2H-1-benzopyran-2-one (compound 14), 3-(1-octenyloxy)-4-hydroxy-7-hexyloxy-2H-1-benzopyran-2-one (compound 15), 3-(1-decenyloxy)-4-hydroxy-7-methoxy-2H-1-benzopyran-2-one (compound 16), 3-(1-hexenyloxy)-4-hydroxy-7-ethoxy-2H-1-benzopyran-2-one (compound 17), 3-prenyloxy-4-hydroxy-7-methoxy-2H-1-benzopyran-2-one (compound 18), 3-prenyloxy-4-hydroxy-7-hexyloxy-2H-1-benzopyran-2-one (compound 19), 3-geranyloxy-4-hydroxy-7-methoxy-2H-1-benzopyran-2-one (compound 20), 3-geranyloxy-4-hydroxy-7-ethoxy-2H-1-benzopyran-2-one (compound 21), 3-ethoxy-4-hydroxy-7-(1-octenyloxy)-2H-1-benzopyran-2-one (compound 22), 3-propoxy-4-hydroxy-7-vinyloxy-2H-1-benzopyran-2-one (compound 23), 3-octyloxy-4-hydroxy-7-vinyloxy-2H-1-benzopyran-2-one (compound 24), 3-ethoxy-4-hydroxy-7-glucopyranosyloxy-2H-1-benzopyran-2-one (compound 25), 3-hexyloxy-4-hydroxy-7-glucopyranosyloxy-2H-1-benzopyran-2-one (compound 26), 3-octyloxy-4-hydroxy-7-glucopyranosyloxy-2H-1-benzopyran-2-one (compound 27), 3-decyloxy-4-hydroxy-7-glucopyranosyloxy-2H-1-benzopyran-2-one (compound 28), 3-hexyloxy-4-hydroxy-7-galactopyranosyloxy-2H-1-benzopyran-2-one (compound 29), 3-octyloxy-4-hydroxy-7-galactopyranosyloxy-2H-1-benzopyran-2-one (compound 30), 3-octyloxy-4-hydroxy-7-mannopyranosyloxy-2H-1-benzopyran-2-one (compound 31), 3-methoxy-4,7-dihydroxy-2H-1-benzopyran-2-one (compound 32), 3-ethoxy-4,7-dihydroxy-2H-1-benzopyran-2-one (compound 33), 3-propoxy-4,7-dihydroxy-2H-1-benzopyran-2-one (compound 34), 3-isopropoxy-4,7-dihydroxy-2H-1-benzopyran-2-one (compound 35), 3-butoxy-4,7-dihydroxy-2H-1-benzopyran-2-one (compound 36), 3-(s-butoxy)-4,7-dihydroxy-2H-1-benzopyran-2-one (compound 37), 3-pentoxy-4,7-dihydroxy-2H-1-benzopyran-2-one (compound 38), 3-(1-ethylpropoxy)-4,7-dihydroxy-2H-1-benzopyran-2-one (compound 39), 3-hexyloxy-4,7-dihydroxy-2H-1-benzopyran-2-one (compound 40), 3-(1-ethylbutoxy)-4,7-dihydroxy-2H-1-benzopyran-2-one (compound 41), 3-(4-methylpentoxy)-4,7-dihydroxy-2H-1-benzopyran-2-one (compound 42), 3-heptyloxy-4,7-dihydroxy-2H-1-benzopyran-2-one (compound 43), 3-octyloxy-4,7-dihydroxy-2H-1-benzopyran-2-one (compound 44), 3-(1-ethylhexyloxy)-4,7-dihydroxy-2H-1-benzopyran-2-one (compound 45), 3-decyloxy-4,7-dihydroxy-2H-1-benzopyran-2-one (compound 46), 3-prenyloxy-4,7-dihydroxy-2H-1-benzopyran-2-one (compound 47), 3-geranyloxy-4,7-dihydroxy-2H-1-benzopyran-2-one (compound 48), 3-(1-butenyloxy)-4-hydroxy-7-methoxy-2H-1-benzopyran-2-one (compound 49), 3-(1-octenyloxy)-4-hydroxy-7-isopropoxy-2H-1-benzopyran-2-one (compound 50), 3-(1-decenyloxy)-4-hydroxy-7-hexyloxy-2H-1-benzopyran-2-one (compound 51), 3-(1-hexenyloxy)-4-hydroxy-7-vinyloxy-2H-1-benzopyran-2-one (compound 52), 3-(1-octenyloxy)-4-hydroxy-7-(1-propenyloxy)-2H-1-benzopyran-2-one (compound 53), 3-(1-hexenyloxy)-4-hydroxy-7-glucopyranosyloxy-2H-1-benzopyran-2-one (compound 54), 3-(1-octenyloxy)-4-hydroxy-7-glucopyranosyloxy-2H-1-benzopyran-2-one (compound 55), 3-(1-decenyloxy)-4-hydroxy-7-glucopyranosyloxy-2H-1-benzopyran-2-one (compound 56), 3-vinyloxy-4,7-dihydroxy-2H-1-benzopyran-2-one (compound 57), 3-(1-hexenyloxy)-4,7-dihydroxy-2H-1-benzopyran-2-one (compound 58), 3-(1-decenyloxy)-4,7-dihydroxy-2H-1-benzopyran-2-one (compound 59), 3-geranyloxy-4,7-dihydroxy-2H-1-benzopyran-2-one (compound 60), 3-vinyloxy-4-hydroxy-7-glucopyranosyloxy-2H-1-benzopyran-2-one (compound 61), 3-(1-hexenyloxy)-4-hydroxy-7-glucopyranosyloxy-2H-1-benzopyran-2-one (compound 62), 3-(1-decenyloxy)-4-hydroxy-7-galactopyranosyloxy-2H-1-benzopyran-2-one (compound 63), 3-geranyloxy-4-hydroxy-7-glucopyranosyloxy-2H-1-benzopyran-2-one (compound 64), 3-vinyloxy-4-hydroxy-7-valeryloxy-2H-1-benzopyran-2-one (compound 65), 3-(1-prenyloxy)-4-hydroxy-7-benzoyloxy-2H-1-benzopyran-2-one (compound 66), 3-ethoxy-4-hydroxy-7-propionyloxy-2H-1-benzopyran-2-one (compound 67), 3-propoxy-4-hydroxy-7-propionyloxy-2H-1-benzopyran-2-one (compound 68), 3-hexyloxy-4-hydroxy-7-acetoxy-2H-1-benzopyran-2-one (compound 69), 3-octyloxy-4-hydroxy-7-acetoxy-2H-1-benzopyran-2-one (compound 70), 3-ethoxy-4-hydroxy-7-(2-acetoxyethoxy)-2H-1-benzopyran-2-one (compound 71), 3-butoxy-4-hydroxy-7-(2-acetoxyethoxy)-2H-1-benzopyran-2-one (compound 72), 3-hexyloxy-4-hydroxy-7-(2-acetoxyethoxy)-2H-1-benzopyran-2-one (compound 73), 3-octyloxy-4-hydroxy-7-(2-acetoxyethoxy)-2H-1-benzopyran-2-one (compound 74), 3-ethoxy-4-hydroxy-7-(2-hydroxyethoxy)-2H-1-benzopyran-2-one (compound 75), 3-butoxy-4-hydroxy-7-(2-hydroxyethoxy)-2H-1-benzopyran-2-one (compound 76), 3-hexyloxy-4-hydroxy-7-(2-hydroxyethoxy)-2H-1-benzopyran-2-one (compound 77), 3-octyloxy-4-hydroxy-7-(2-hydroxyethoxy)-2H-1-benzopyran-2-one (compound 78), 3-ethoxy-4-hydroxy-7-(2,2-dimethyl-1,3-dioxolane-4-methoxy)-2H-1-benzopyran-2-one (compound 79), 3-butoxy-4-hydroxy-7-(2,2-dimethyl-1,3-dioxolane-4-methoxy)-2H-1-benzopyran-2-one (compound 80), 3-hexyloxy-4-hydroxy-7-(2,2-dimethyl-1,3-dioxolane-4-methoxy)-2H-1-benzopyran-2-one (compound 81), 3-octyloxy-4-hydroxy-7-(2,2-dimethyl-1,3-dioxolane-4-methoxy)-2H-1-benzopyran-2-one (compound 82), 3-ethoxy-4-hydroxy-7-glyceroxy-2H-1-benzopyran-2-one (compound 83), 3-butoxy-4-hydroxy-7-glyceroxy-2H-1-benzopyran-2-one (compound 84), 3-hexyloxy-4-hydroxy-7-glyceroxy-2H-1-benzopyran-2-one (compound 85), 3-octyloxy-4-hydroxy-7-glyceroxy-2H-1-benzopyran-2-one (compound 86), 3-ethoxy-4-hydroxy-7-(3-acetoxypropoxy)-2H-1-benzopyran-2-one (compound 87), 3-butoxy-4-hydroxy-7-(3-acetoxypropoxy)-2H-1-benzopyran-2-one (compound 88), 3-hexyloxy-4-hydroxy-7-(3-acetoxypropoxy)-2H-1-benzopyran-2-one (compound 89), 3-octyloxy-4-hydroxy-7-(3-acetoxypropoxy)-2H-1-benzopyran-2-one (compound 90), 3-ethoxy-4-hydroxy-7-(3-hydroxypropoxy)-2H-1-benzopyran-2-one (compound 91), 3-butoxy-4-hydroxy-7-(3-hydroxypropoxy)-2H-1-benzopyran-2-one (compound 92), 3-hexyloxy-4-hydroxy-7-(3-hydroxypropoxy)-2H-1-benzopyran-2-one (compound 93), 3-octyloxy-4-hydroxy-7-(3-hydroxypropoxy)-2H-1-benzopyran-2-one (compound 94), 3-ethoxy-4-hydroxy-7-(4-acetoxybutoxy)-2H-1-benzopyran-2-one (compound 95), 3-butoxy-4-hydroxy-7-(4-acetoxybutoxy)-2H-1- benzopyran-2-one (compound 96), 3-hexyloxy-4-hydroxy-7-(4-acetoxybutoxy)-2H-1-benzopyran-2-one (compound 97), 3-octyloxy-4-hydroxy-7-(4-acetoxybutoxy)-2H-1-benzopyran-2-one (compound 98), 3-ethoxy-4-hydroxy-7-(4-hydroxybutoxy)-2H-1-benzopyran-2-one (compound 99), 3-butoxy-4-hydroxy-7-(4-hydroxybutoxy)-2H-1-benzopyran-2-one (compound 100), 3-hexyloxy-4-hydroxy-7-(4-hydroxybutoxy)-2H-1-benzopyran-2-one (compound 101), 3-octyloxy-4-hydroxy-7-(4-hydroxybutoxy)-2H-1-benzopyran-2-one (compound 102), 3-ethoxy-4-hydroxy-7-(2,2-dimethyl-1,3-dioxolane-4-ethoxy)-2H-1-benzopyran-2-one (compound 103), 3-butoxy-4-hydroxy-7-(2,2-dimethyl-1,3-dioxolane-4-ethoxy)-2H-1-benzopyran-2-one (compound 104), 3-hexyloxy-4-hydroxy-7-(2,2-dimethyl-1,3-dioxolane-4-ethoxy)-2H-1-benzopyran-2-one (compound 105), 3-octyloxy-4-hydroxy-7-(2,2-dimethyl-1,3-dioxolane-4-ethoxy)-2H-1-benzopyran-2-one (compound 106), 3-ethoxy-4-hydroxy-7-(3,4-dihydroxybutoxy)-2H-1-benzopyran-2-one (compound 107), 3-butoxy-4-hydroxy-7-(3,4-dihydroxybutoxy)-2H-1-benzopyran-2-one (compound 108), 3-hexyloxy-4-hydroxy-7-(3,4-dihydroxybutoxy)-2H-1-benzopyran-2-one (compound 109), 3-octyloxy-4-hydroxy-7-(3,4-dihydroxybutoxy)-2H-1-benzopyran-2-one (compound 110)

And physiologically acceptable salts of these compounds are also included in the illustrative examples. The term "physiologically acceptable salts" as used herein means nontoxic alkali addition salts of, for example, the compounds cited above, which include sodium salts, potassium salts, magnesium salts, calcium salts, ammonium salts, nontoxic amine salts and the like. These physiologically acceptable salts can be produced by known methods and are also included in the present invention.

The benzopyran derivatives and physiologically acceptable salts thereof of the present invention (to be referred to as "the compound of the present invention" hereinafter) are, as will be described later in examples, useful for the treatment or prevention of various heart diseases such as ischemic heart disease, arrhythmia and the like.

The heart diseases cited in the present invention are, for example, supraventricular extrasystoles, paroxysmal supraventricular tachycardia, paroxysmal atrial fibrillation, chronic atrial fibrillation, atrial fibrillation, ventricular extrasystoles, ventricular tachycardia, arrhythmia (such as atrial fibrillation and auriculoventricular block and the like), ischemic heart disease, myocardial infarction, arrhythmia derived from angina pectoris, acute myocardial infarction, chronic myocardial infarction, heart failure, angina pectoris and the like.

The treatment medicine for heart diseases which comprises the compound of the present invention as an active ingredient can be administered orally or parenterally (for example, intravenous injection, subcutaneous injection, percutaneous absorption, rectal administration or the like). Such a pharmaceutical agent can be made into various dosage forms according to the purpose, such as tablets, capsules, granules, fine subtilaes, powders, troches, sublingual tablets, suppositories, ointments, injections, emulsions, suspensions, medicated syrups and the like.

These dosage forms can be prepared in accordance with known techniques making use of pharmaceutically acceptable carriers which are commonly used in this type of drugs, such as excipients, bonding agents, disintegrators, lubricants, preservatives, anti-oxidative agents, isotonic agents, buffering agents, coating agents, sweetening agents, dissolving agents, bases, dispersing agents, stabilizing agents, coloring agents and the like. Ilustrative examples of these pharmaceutically acceptable carriers are listed in the following.

Firstly, as excipients, the following can be listed: starch and derivatives of starch (such as dextrin, carboxymethyl starch and the like), cellulose and derivatives of cellulose (such as methylcellulose, hydroxypropylmethylcellulose and the like), sugars (such as lactose, sucrose, glucose and the like), silicic acid and silicates (such as naturally occurring aluminum silicate, magnesium silicate and the like), carbonates (such as calcium carbonate, magnesium carbonate, sodium hydrogencarbonate and the like), aluminum magnesium hydroxide, synthetic hydrotalcite, polyoxyethylene derivatives, glycerin monostearate, sorbitan monooleic acid and the like.

As bonding agents, the following can be listed: starch and starch derivatives (such as alpha starches, dextrin and the like), cellulose and derivatives of cellulose (such as ethyl cellulose, sodium carboxymethyl cellulose, hydroxypropylmethyl cellulose and the like), gum arabic, traganth, gelatin, sugars (such as glucose, sucrose and the like), ethanol, polyvinyl alcohols and the like.

As disintegrators, the following can be listed: starch and starch derivatives (such as carboxymethyl starch, hydroxypropyl starch and the like), cellulose and cellulose derivatives (such as sodium carboxymethyl cellulose, crystal cellulose, hydroxypropylmethyl cellulose and the like), carbonates (such as calcium carbonate, calcium hydrogencarbonate and the like), traganth, gelatins, agar and the like.

As lubricants, the following can be listed: stearic acid, calcium stearate, magnesium stearate, talc, silicic acid and its salts (such as light slicic anhydrides, naturally occurring aluminum silicates and the like), titanium oxide, calcium hydrogen phosphate, dry aluminum hydroxide gel, macrogol and the like.

As preservatives, the following can be listed: p-hydroxybenzoates, sulfites (such as sodium sulfites, sodium pyrosulfites and the like), phosphates (such as sodium phosphates, calcium polyphosphates, sodium polyphosphates, sodium methaphosphate and the like), alcohols (such as chlorobutanol, benzyl alcohol and the like), benzalkonium chloride, benzethonium chloride, phenol, cresol, chlorocresol, dihydroacetic acid, sodium dihydroacetate, glycerin sorbic acid, sugars and the like.

As anti-oxidative agents, the following can be listed: sulfites (such as sodium sulfite, sodium hydrogen sulfite and the like), rongalite, erythorbic acid, L-ascorbic acid, cysteine, thioglycerol, butylhydroxyanisol, dibutylhydroxytoluene, propylgallic acid, ascorbyl palmitate, dl-α-tocopherol and the like.

As isotonic agents, the following can be listed: sodium chloride, sodium nitrate, potassium nitrate, dextrin, glycerin, glucose and the like.

As buffering agents, the following can be listed: sodium carbonate, hydrochloric acid, boric acid, phosphates (such as sodium hydrogenphosphate) and the like.

As coating agents, the following can be listed: cellulose derivatives (such as hydroxypropyl cellulose, cellulose acetate phthalate, hydroxypropylmethyl cellulose phthalate and the like), shellac, polyvinylpyrrolidone, polyvinylpyridines (such as poly-2-vinylpyridine, poly-2-vinyl-5-ethylpyridine and the like), polyvinylacetyl diethylaminoacetate, polyvinyl alcohol phthalate, methacrylate, methacrylate copolymers and the like.

As sweetening agents, the following can be listed: sugars (such as glucose, sucrose, lactose and the like), sodium saccharin, sugar alcohols and the like.

As dissolving agents, the following can be listed: ethylenediamine, nicotinamide, sodium saccharin, citric acid, citrates, sodium benzoic acid, soaps, polyvinylpyrrolidone, polysolvates, sorbitan fatty acid esters, glycerin, propylene glycol, benzyl alcohols and the like.

As bases, the following can be listed: fats (such as lard and the like), vegetable oils (such as olive oil, sesame oil and the like), animal oil, lanolin acid, petrolatums, paraffin, wax, resins, bentonite, glycerin, glycol oils, higher alcohols (such as stearyl alcohol, cetanol) and the like.

As dispersing agents, the following can be listed: gum arabic, traganth, cellulose derivatives (such as methyl cellulose and the like), stearic acid polyesters, sorbitan sesquioleate, aluminum monostearate, sodium alginate, polysolvates, sorbitan fatty acid esters and the like.

Lastly, as stabilizing agents, the following can be listed: sulfites (such as sodium hydrogen sulfite and the like), nitrogen, carbon dioxide and the like.

Though the content of the compound of the present invention in these pharmaceutical preparations varies depending on the dosage forms, it may be contained preferably in a concentration of from 0.01 to 100% by weight.

Dose of the treatment medicine for heart disease of the present invention can be varied over a broad range depending on each warm-blooded animal including human and the like, to be treated, extent of each disease, doctor's judgement and the like. In general, however, it may be administered in a dose of from 0.01 to 50 mg, preferably from 0.05 to 10 mg, as the active ingredient per day per kg body weight in the case of oral administration or in a dose of from 0.01 to 10 mg, preferably from 0.01 to 5 mg, as the active ingredient per day per kg body weight in the case of parenteral administration. The daily dose described above may be used in one portion or in divided portions and changed optionally in accordance with the extent of diseases and doctor's judgement.

EXAMPLES

The following examples are intended to illustrate this invention, however these examples are intended to illustrate the invention and not to be construed to limit the scope of the invention. First examples of preparation of the new benzopyran derivatives of the present invention, and next results of pharmacological tests of the compounds of the present invention will be cited.

Example 1

3-octyloxy-4-hydroxy-7-(2-acethoxyethoxy)-2H-1-benzopyran-2-one (compound 74)

To a solution of 2.24 g of potassium t-butoxide (0.02 mol) in 4.0 ml of DMF was dropped 3.06 g of 3-octyloxy-4,7-dihydroxy-2H-1-benzopyran-2-one (0.01 mol) in 16.0 ml of DMF at 15~25°, and the mixture was stirred for 30 minutes. To this mixture was added 1.67 g of 2-bromoethyl acetate (0.01 mol) and stirred at the same temperature for 3 hours. The reaction mixture was poured into 105 ml of 3N-HCl, extracted with ethyl acetate (50 ml×2), and dried over $MgSO_4$. After filtration, the filtrate was concentrated under reduced pressure to give 5.39 g of a crude product. Purification of the obtained crude by silica gel column chromatography (eluent:hexane/ethyl acetate=2/1) gave 2.94 g of the title compound. (Yield:75%)

H-NMR ($CDCl_3$, δ-TMS): 7.71 (d, 1 H, J=8.8 Hz), 7.20 (bs, 1H), 6.91 (dd, 1 H, J=8.8 Hz,, J=2.4 Hz), 6.81 (d, 1H, J=2.4 Hz), 4.46 (t, 2 H, J=5.2 Hz), 4.23 (t, 2 H, J=5.2 Hz), 4.15 (t, 2 H, J=6.8 Hz), 2.12 (s, 3H), 1.74 (m, 2H), 1.41~1.20 (m, 10H), 0.87 (t, 3 H, J=7.2Hz) IR (KBr, $cm^{-1}$):3300, 3005, 1725, 1600, 1230

Elemental analysis for $C_{21}H_{28}O_7$ Calculated (%):C 64.27, H 7.19, O 28.54 Found (%):C 64.38, H 7.28, O 28.34

Example 2

3-octhyloxy-4-hydroxy-7-(2-hydroxyethoxy)-2H-1-benzopyran-2-one (compound 78)

3.92 g of 3-octyloxy-4-hydroxy-7-(2-acetoxyethoxy)-2H-1-benzopyran-2-one (0.01 mol) was added to 20 ml of 1N-NaOH solution and the mixture was stirred at room temperature for 30 minutes. The reaction mixture was neutralized with 105 ml of 0.2N-HCl solution and extracted with ethyl acetate. The organic layer was concentrated under reduced pressure, giving a crude product. This crude was purified by silica gel column chromatography (eluent:hexane/acetone=2/1), followed by recrystallizing (from ethyl acetate/hexane=3/10) to afford 2.87 g of the title compound. (Yield:82 %)

$^1$H-NMR (DMSO-$d_6$, δ-TMS): 11.50 (bs,1 H), 7.70 (d, 1H, J=7.2 Hz), 6.95 (s, 2H), 4.91 (bs, 1H), 4.07 (t, 2 H, J=6.8. Hz), 3.88 (t, 2 H, J=5.2 Hz), 3.73 (t, 2 H, J=5.2 Hz), 1.68 (m, 2H), 1.40~1.25 (m, 10H), 0.86 (t, 3 H, J=7.2 Hz) IR (KBr, $cm^{-1}$):3300, 3005, 1670, 1600, 1230

Elemental analysis for $C_{19}H_{26}O_6$ Calculated (%):C 65.12H 7.48, O 27.40 Found (%):C 65.48, H 7.18, O 27.34

Example 3

3-butoxy-4-hydroxy-7-(2-acetoxyethoxy)-2H-1-benzopyran-2-one (compound 72)

In accordance with EXAMPLE 1, 3-butoxy-4,7-dihydroxy-2H-1-benzopyran-2-one was used instead of 3-octyloxy-4,7-dihydroxy-2H-1-benzopyran-2-one, the title compound was obtained.

$^1$H-NMR ($CDCl_3$, δ-TMS): 7.73 (d, 1 H, J=8.8 Hz), 7.21 (bs, 1H), 6.90 (dd, 1 H, J=8.8 Hz,, J=2.4 Hz), 6.81 (d, 1 H, J=2.4 Hz), 4.46 (t, 2 H, J=5.2 Hz), 4.18 (t, 2 H, J=5.2 Hz), 4.15 (t, 2 H, J=6.8 Hz), 2.15 (s, 3H), 1.74~1.20 (m, 4H), 0.92 (t, 3 H, J=7.2 Hz) IR (KBr, $cm^{-1}$):3300, 3005, 1725, 1600, 1230

Elemental analysis for $C_{17}H_{20}O_7$ Calculated (%):C 60.71, H 5.99, O 33.30 Found (%):C 60.58, H 5.98, O 33.44

Example 4

3-butoxy-4-hydroxy-7-(2-hydroxyethoxy)-2H-1-benzopyran-2-one (compound 76)

In accordance with EXAMPLE 2, 3-butoxy-4-hydroxy-7-(2-acetoxyethoxy)-2H-1-benzopyran-2-one was used instead of 3-octyloxy-4-hydroxy-7-(2-acetoxyethoxy)-2H-1-benzopyran-2-one, the title compound was obtained.

$^1$H-NMR (DMSO-$d_6$, δ-TMS): 11.45 (bs, 1H), 7.72 (d, 1 H, J=7.2 Hz), 6.90 (s, 2H), 4.86 (bs, 1H), 4.07 (t, 2 H, J=6.8 Hz), 3.88 (t, 2 H, J=5.2 Hz), 3.78 (t, 2 H, J=5.2 Hz), 1.68~1.25 (m, 4H), 0.86 (t, 3 H, J=7.2 Hz) IR (KBr, $cm^{-1}$):3300, 3005, 1670, 1600, 1230

Elemental analysis for $C_{15}H_{18}O_6$ Calculated (%):C 61.21, H 6.17, O 32.62 Found (%):C 61.38, H 6.18, O 32.44

Example 5

3-octyloxy-4-hydroxy-7-(2,2-dimethyl-1,3-dioxolane-4-methoxy)-2H-1-benzopyran-2-one (compound 82)

To a solution of 2.24 g of potassium t-butoxide (0.02 mol) in 4.0 ml of DMF was dropped 3.06 g of 3-octyloxy-4,7-dihydroxy-2H-1-benzopyran-2-one (0.01 mol) in 16.0 ml of DMF at 15~25°, and the mixture was stirred for 30 minutes. To this mixture was added 2.86 g of 2,2-dimethyl-1,3-dioxolane-4-ylmethyl p-toluenesulfonate (0.01 mol) and stirred at the same temperature for 3 hours. The reaction mixture was poured into 105 ml of 3N-HCl, extracted with ethyl acetate (50 ml×2), and dried over MgSO$_4$. After filtration, the filtrate was concentrated under reduced pressure to give a crude product. Purification of the obtained crude by silica gel column chromatography (eluent:hexane/ethyl acetate=2/1) gave 2.86 g of the title compound. (Yield:68%)

$^1$H-NMR (CDCl$_3$, δ-TMS): 7.69 (d, 1 H, J=8.8 Hz), 7.14 (bs, 1H), 6.92 (dd, 1 H, J=8.8 Hz,, J=2.4 Hz), 6.82 (d, 1 H, J=2.4 Hz), 4.52 (t, 2 H, J=5.2 Hz), 4.21~3.90 (m, 5H), 1.75 (m, 2H), 1.48 (s, 3H), 1.42 (s, 3H), 1.41~1.20 (m, 10 H), 0.87 (t, 3 H, J=7.2 Hz) IR (KBr, cm$^{-1}$):3300, 3005, 1725, 1600, 1230

Elemental analysis for C$_{23}$H$_{32}$O$_7$ Calculated (%):C 65.69, H 7.67, O 26.64 Found (%):C 65.68, H 7.48, O 26.84

Example 6

3-octyloxy-4-hydroxy-7-glyceroxy-2H-1-benzopyran-2-one (compound 86)

2.36 g of 3-octyloxy-4-hydroxy-7-(2,2-dimethyl-1,3-dioxolane-4-methoxy)-2H-1-benzopyran-2-one (5.46 mmol) was added to 23 ml of 80% acetic acid and the mixture was stirred at 60° for 4 hours. The reaction mixture was evaporated under reduced pressure, giving a crude product. The obtained crude was recrystallized from methanol to yield 1.30 g of the title compound. (Yield:62%)

$^1$H-NMR (DMSO-d$_6$, δ-TMS): 11.51 (bs, 1H), 7.70 (d, 1 H, J=8.8 Hz), 6.95 (m, 2H), 5.00 (s, 1H), 4.70 (s, 1 H), 4.11~3.81 (m, 5H), 3.45 (s, 2H), 1.69 (m, 2H), 1.40~1.18 (m, 10 H), 0.86 (t, 3 H, J=7.2 Hz) IR (KBr, cm$^{-1}$):3420, 3005, 1680, 1610, 1260

Elemental analysis for C$_{20}$H$_{28}$O$_7$ Calculated (%):C 63.14, H 7.42, O 29.44 Found (%):C 63.38, H 7.58, O 29.04

Example 7

3-butoxy-4-hydroxy-7-(2,2-dimethyl-1,3-dioxolane-4-methoxy)-2H-1-benzopyran-2-one (compound 80)

In accordance with EXAMPLE 5, 3-butoxy-4,7-dihydroxy-2H-1-benzopyran-2-one was used instead of 3-octyloxy-4,7-dihydroxy-2H-1-benzopyran-2-one, the title compound was obtained.

$^1$H-NMR (CDCl$_3$, δ-TMS): 7.72 (d, 1 H, J=8.8 Hz), 7.11 (bs, 1H), 6.92 (dd, 1 H, J=8.8 Hz,, J=2.4 Hz), 6.83 (d, 1 H, J=2.4 Hz), 4.52 (t, 2 H, J=5.2 Hz), 4.21~3.90 (m, 5H), 1.75 (m, 2H), 1.45 (s, 3H), 1.41 (s, 3H), 1.37~1.20 (m, 2H), 0.88 (t, 3 H, J=7.2 Hz) IR (KBr, cm$^{-1}$):3300, 3005, 1725, 1600, 1230

Elemental analysis for C$_{19}$H$_{24}$O$_7$ Calculated (%):C 62.62, H 6.64, O 30.73 Found (%):C 62.68, H 6.58, O 30.74

Example 8

3-butoxy-4-hydroxy-7-glyceroxy-2H-1-benzopyran-2-one (compound 84)

In accordance with EXAMPLE 6, 3-butoxy-4-hydroxy-7-(2,2-dimethyl-1,3-dioxolane-4-methoxy)-2H-1-benzopyran-2-one was used instead of 3-octyloxy-4-hydroxy-7-(2,2-dimethyl-1,3-dioxolane-4-methoxy)-2H-1-benzopyran-2-one, the title compound was obtained.

$^1$H-NMR (DMSO-d$_6$, δ-TMS): 11.49 (bs, 1H), 7.70 (d, 1 H, J=8.8 Hz), 6.95 (m, 2H), 5.00(s, 1H), 4.70 (s, 1H), 4.08~3.75 (m, 5H), 3.45 (s, 2H), 1.69 (m, 2H), 1.23~1.18 (m, 2 H, 0.88 (t, 3 H, J=7.2 Hz) IR (KBr, cm$^{-1}$):3420, 3005, 1680, 1610, 1260

Elemental analysis for C$_{16}$H$_{20}$O$_7$ Calculated (%):C 59.25, H 6.22, O 34.53 Found (%):C 59.35, H 6.28, O 34.37

Example 9

Acute Toxicity Test in Mice

We performed this test in order to confirm the low toxicity of the compounds of the present invention. Each of suspensions of benzopyran derivatives (compound No. 1~110) in 0.5% methyl cellulose was forcibly administered orally at the doses of 1000 and 2000 mg/kg to male ICR mice (body weight is 20~25 g, 5 mice per one group), using an esophageal sound. After the administration, the animals were kept in cages for 7 days, to observed general symptoms and to count dead animals. Lethal dose (LD$_{50}$:mg/kg) was extrapolated from the mortality at 7th day after administration.

In result, the LD$_{50}$ of all compounds were over 1000 mg/kg, and therefore it was clearly shown that the compounds of the present invention, benzopyran derivatives, have extremely low toxicity.

Example 10

Pharmacological Test by Ouabain-induced Arrhythmia Model in Guinea Pigs

In order to confirm the effectiveness of the compound of the present invention in treating heart disease, a pharmacological test was performed by using a ouabain-induced arrhythmia model which is widely used to evaluate the pharmacological effectiveness of anti-arrhythmic agents (Compilation of Animal Models Used for Development of New Pharmaceuticals, R & D Planning, p. 166, 1985).

Guinea pigs (genus Hartley, six weeks old) were anesthetized by urethane, after which lead electrodes were applied to their hindlegs and forelegs, and the electrocardiograms at the standard second leads were recorded and analyzed by means of an animal electrocardiogram analysis system (ECG-01, manufactured by Japan Energy Kabushiki Kaisha). After confirming that the waveform and heart rate in the electrocardiograms were within the normal range, the epidermis of the jugular was cut open for trachea intubation, then the left external jugular vein and the left common jugular vein were cannulated with polyethylene tubes.

Immediately after administering the compound of the present invention as a 15% DMSO (dimethylsulfoxide) solution using a syringe through the right external jugular vein, ouabain was continually administered at a rate of 3 μg/0.1 ml/minute through the polyethylene tube cannulated in the left external jugular vein using a syringe pump (Atom Syringe Pump 1235, manufactured by Atom Kabushiki Kaisha).

Additionally, the polyethylene tube cannulated in the left common jugular vein was connected to a Pressure Transducer (P23XL, Gould Electronics) and led to a Pressure Processor Signal Conditioner (Gould Electronics) to record the blood pressure and heart rate on a Thermal Array Recorder (TA-11, Gould Electronics).

The effects were evaluated by comparing the dosage of ouabain administered (μg/kg) until the onset of arrhythmia and the occurrence of cardiac arrest (if the anti-arrhythmic effects are high, then arrhythmia will not be induced even if large amount of ouabain are administered). The guinea pigs were divided into a solvent-administered group (administered with the same amount of DMSO solution as the test drug group) and a group administered with disopyramide phosphate (15% DMSO solution) which is a typical anti-arrhythmic agent as a positive control group. The test results are shown in Tables 1–3.

TABLE 1

| Compound No. | Dosage (mg/kg) | Total Ouabain Dosage (µg/kg) | |
|---|---|---|---|
| | | Cardiac Arrhythmia | Cardiac Arrest |
| 4 | 3 | 158 | 198 |
| 10 | 3 | 161 | 212 |
| 11 | 3 | 157 | 199 |
| 12 | 3 | 169 | 233 |
| 13 | 3 | 166 | 222 |
| 14 | 3 | 156 | 208 |
| 15 | 3 | 159 | 199 |
| 16 | 3 | 153 | 204 |
| 17 | 3 | 162 | 211 |
| 22 | 3 | 159 | 208 |
| 23 | 3 | 151 | 201 |
| 24 | 3 | 163 | 238 |
| 25 | 3 | 167 | 240 |
| 26 | 3 | 171 | 254 |
| 27 | 3 | 177 | 262 |
| 28 | 3 | 168 | 251 |

TABLE 2

| Compound No. | Dosage (mg/kg) | Total Ouabain Dosage (µg/kg) | |
|---|---|---|---|
| | | Cardiac Arrhythmia | Cardiac Arrest |
| 30 | 3 | 163 | 247 |
| 31 | 3 | 166 | 248 |
| 34 | 3 | 163 | 215 |
| 36 | 3 | 158 | 222 |
| 37 | 3 | 164 | 219 |
| 40 | 3 | 178 | 256 |
| 44 | 3 | 182 | 277 |
| 46 | 3 | 160 | 249 |
| 53 | 3 | 167 | 203 |
| 54 | 3 | 164 | 237 |
| 55 | 3 | 169 | 241 |
| 56 | 3 | 160 | 226 |
| 57 | 3 | 168 | 206 |
| 58 | 3 | 165 | 218 |
| 59 | 3 | 166 | 210 |
| 65 | 3 | 155 | 193 |

TABLE 3

| Compound No. | Dosage (mg/kg) | Total Ouabain Dosage (µg/kg) | |
|---|---|---|---|
| | | Cardiac Arrhythmia | Cardiac Arrest |
| 66 | 3 | 150 | 187 |
| 67 | 3 | 162 | 215 |
| 68 | 3 | 164 | 230 |
| 69 | 3 | 156 | 221 |
| 70 | 3 | 162 | 226 |
| 74 | 3 | 178 | 223 |
| 78 | 3 | 176 | 219 |
| 86 | 3 | 168 | 208 |
| 94 | 3 | 178 | 222 |
| 100 | 3 | 181 | 235 |
| 106 | 3 | 170 | 215 |
| 110 | 3 | 174 | 220 |
| Disopyramide Phosphate | 3.9 | 176 | 247 |
| Solvent-administered Group | — | 132 | 176 |

As shown in Tables 1 through 3, with the group administered the solvent, cardiac arrhythmia was induced total dosage of 132 µg/kg ouabain, which then resulted in cardiac arrest at 176 µg/kg. In contrast, the administration of 3.9 mg/kg of disopyramide phosphate which is a typical antiarrhythmic agent (3.0 mg/kg as disopyramide, in a 15% DMSO solution) resulted in increases of threshold values in the cardiac arrhythmia and cardiac arrest induction, which are respectively 176 µg/kg and 247 µg/kg, thus confirming that disopyramide phosphate has antiarrhythmic activity.

On the other hand, with the administration of the compound of the present invention, an increase on threshold values in the cardiac arrhythmia and cardiac arrest were equal to or greater than that of disopyramide phosphate. As demonstrated by this example, the compound of the present invention has antiarrhythmic activity of equal to or greater than that of commercially available antiarrhythmic agents, and is useful as a heart disease treating agent.

Example 11
Analysis of Arrhythmia Induction Effect in Guinea Pigs

Pharmaceuticals for treating heart disease, especially antiarrhythmic agents, often exhibit heart toxicity as side effects, and disopyramide phosphate which was used as a positive control in Example 10 is known to have a proarrhythmic effect as well as an antiarrhythmic effect (Iyakuhin Yoran, 5th Edition, Osaka-fu Hospital Pharmacists' Society, page 543, 1992).

In the present example, the presence or non-presence of the induction of cardiac arrhythmia or cardiac arrest was observed one hour or more after administration of disopyramide phosphate or the compound of the present invention only, without administering ouabain. The results are shown in Table 4.

TABLE 4

| Compound No. | Dosage (mg/kg) | Arrhythmia | Cardiac Arrest |
|---|---|---|---|
| 36 | 3 | No | No |
| 36 | 10 | No | No |
| 44 | 3 | No | No |
| 44 | 10 | No | No |
| 55 | 3 | No | No |
| 55 | 10 | No | No |
| 78 | 3 | No | No |
| 78 | 10 | No | No |
| Disopyramide Phosphate | 3.9 | No | No |
| Disopyramide Phosphate | 12.9 | — | Yes |

As shown in Table 4, immediately after administering 12.9 mg/kg of disopyramide phosphate (10 mg/kg as disopyramide), cardiac arrest occurred almost without time to confirm the occurrence of arrhythmia, so that the difference between an effective dose and a toxic dose was extremely narrow. In contrast, toxicity was not observed even when 3 or 10 mg/kg of compounds 36, 44, 55 and 78 of the present invention were administered, thereby demonstrating safety even at 10 mg/kg, approximately three times the effective dose of 3 mg/kg.

Example 12
Pharmacological Test by Myocardial Disorder Model Induced by Ischemia in Dogs In order to confirm the effectiveness of the compounds of the present invention with respect to myocardial infarction and arrhythmia caused by myocardial infarction, a pharmacological test was performed by means of a myocardial disorder model induced by ischemia reperfusion using dogs.

A dog having a body weight of approximately 10 kg was anesthetized by pentobarbital (30 mg/ml/kg), then artificial respiration was started and the surgery portion was shaved. The femur vein and femur artery were detached and cannulated. The femur vein was made into a route for administering the test drugs, and the femur artery was used to measure blood pressure. Next, the left chest was opened, the cardiac vesicle membrane was cut, and after exposing the left ventricle, the left coronary artery was detached. An occlussive floss was passed through the coronary artery, and an electromagnetic flowmeter probe for measuring the blood flow was attached.

Additionally, a pair of ultrasonic crystal probes were affixed in order to measure the changes in the ventricle wall length as myocardial constriction. 3 mg/kg of the compound of the present invention (15% DMSO solution) were administered through the femur vein, the coronary artery was sealed 10 minutes thereafter for 20 minutes, then the coronary artery was reperfused. The myocardial constriction force for each group was compared with the myocardial constriction force prior to ischemia reperfusion as 100. Also, these were compared with a solvent-administered group administered with only DMSO solution. The results are shown in Table 5.

TABLE 5

| Compound No. | Dosage (mg/kg) | Myocardial Constriction Force (%) (at 100% prior to ischemia) |
|---|---|---|
| 24 | 3 | 54 |
| 30 | 3 | 78 |
| 36 | 3 | 80 |
| 40 | 3 | 65 |
| 44 | 3 | 82 |
| 55 | 3 | 62 |
| 78 | 3 | 81 |
| Solvent-administered Group | — | 26 |

As shown in Table 5, in the solvent-administered group, the myocardial constriction force dropped to 26% due to ischemia reperfusion. In contrast, the myocardial constriction was 58–82% that prior to reperfusion in the group administered the compound of the present invention, thus clearly reducing the disorder effects of ischemia reperfusion. The model of the present experiment is an experimental model of myocardial disorders due to myocardial infarction and myocardial disorders occurring during reperfusion of blood flow to the myocardial area which is a serious clinical problem (Compilation of Animal Models Used for Development of New Pharmaceuticals, R & D Planning, p. 167, 1985), and the present example makes clear that the compound of the present invention is a heart disease treating agent which is useful in the treatment of myocardial infarction and myocardial disorders accompanying myocardial infarction.

Example 13
Pharmacological Test by Myocardial Disorder Model Induced by Ischemia in Rats Next, a pharmacological test was performed by means of a myocardial disorder model induced by ischemia using rats. Rats were affixed in a supine position under anesthesia due to administration of 55 mg/kg of sodium pentobarbital by an intraperitoneal injection, then the jugular area was cut open and a tube for artificial respiration was inserted into the trachea, then a artificial respirator (SN-480-7, Shinano) was put into operation (1.5 cc/100 g: 50 beats/minute). The blood pressure was measured by inserting a cannule for measuring blood pressure into the right femur artery and measuring through a Pressure Strain Gauge (AP-641G, Nippon Koden) and a Pressure Transducer (P23XL-1, Nippon Koden).

Additionally, a cannule for administering pharmaceuticals was inserted into the right femur artery, then a second lead electrode electrocardiogram was measured through an Electrocardiograph (JB-101J, AB-651J, Nippon Koden) with electrodes attached to the foreleg and hindleg. The heart rate was measured by a Heart Rate Meter (AT-601G, Nippon Koden) from the electrocardiograph waveform, while maintaining the body temperature at 36.5±0.5° C. using a warming lamp.

Next, the fifth intercostal was opened and the cardiac vesicle membrane was cut to expose the heart, the heart was taken outside the thoracic cavity by using a ringed pin set, a threaded suture needle was thrust into the muscle of the pulmonary artery cone and passed underneath the ramus descendes of the left coronary artery, after which the heart was immediately returned within the thoracic cavity. A thread for ligation was passed through a polyethylene tube and prepared for ligation. After allowing the sample to stabilize for 30 minutes, the compound of the present invention (15% DMSO solution) was administered into the vein.

After 5 minutes of test compound administration, the polyethylene tube through which was passed the thread around the coronary artery was pulled back and affixed by a mosquito forceps so as to ligate the coronary artery. After 5 minutes of ligation, reperfusion was performed for 5 minutes. The test used eight rats for each group, and the evaluation was made according to the occurrence of ventricular fibrillation and death rate after 5 minutes of reperfusion among these groups. The results are shown in Table 6.

TABLE 6

| Compound No. | Dosage (mg/kg) | Occurrence of Ventricular Fibrillation (%) | Death Rate (%) |
|---|---|---|---|
| 7 | 3 | 37.5 | 37.5 |
| 10 | 3 | 25.0 | 25.0 |
| 26 | 3 | 25.0 | 25.0 |
| 27 | 3 | 25.0 | 25.0 |
| 36 | 3 | 12.5 | 12.5 |
| 40 | 3 | 25.0 | 25.0 |
| 44 | 3 | 25.0 | 12.5 |
| 46 | 3 | 37.5 | 25.0 |
| 47 | 3 | 37.5 | 25.0 |
| 76 | 3 | 25.0 | 25.0 |
| 78 | 3 | 12.5 | 12.5 |
| 86 | 3 | 37.5 | 25.0 |
| Lidocaine | 3 | 37.5 | 12.5 |
| Solvent-administered Group | — | 100 | 87.5 |

As shown in Table 6, ventricular fibrillation occurred as a result of disorder induced by ischemia reperfusion 100% of the time and the death rate was a high 87.5% in the case of the solvent-administered group (pharmaceutical non-administered group). Additionally, the lidocaine-administered group (administered in the form of a 15% DMSO solution) which was a positive control group exhibited inhibitory effects of 37.5% and 12.5% each.

In contrast, the group which was administered the compound of the present invention exhibited effects equal to or greater than those of the lidocaine-administered group which was the positive control group, thus it is clear from the present example that the compound of the present invention is a heart disease treating pharmaceutical which is useful in the treatment of myocardial infarction and myocardial disorders accompanying cardiac infarction.

Example 14

(5% Powders)

Crystals of 50 mg of the compound 7 were pulverized in a mortar and 950 mg of lactose was added. The mixture was thoroughly mixed by pulverizing with a pestle to obtain 5% powders.

Example 15

(5% Powders)

5% powders were obtained in a similar manner as EXAMPLE 14 by using 50 mg of the compound 10 and 950 mg of lactose.

Example 16

(10% Granules)

300 mg of the compound 26 was mixed with 300 mg of starch and pulverized in a mortar. This was further mixed with 2000 mg of lactose and 370 mg of starch. Separately from this, 30 mg of gelatin was mixed with 1 ml of purified water, solubilized by heating, cooled and then, with stirring, mixed with 1 ml of ethanol to prepare a gelatin solution. Thereafter, the mixture prepared above was mixed with the gelatin solution, and the resulting mixture was kneaded, granulated and then dried to obtain granules.

Example 17

(10% Granules)

10% granules were obtained in a similar manner as EXAMPLE 16 by using 300 mg of the compound 27.

Example 18

(5 mg of Tablets)

To give 100 mg/tablet at the ratio of which 5 mg of compound 10, 62 mg of lactose, 30 mg of starch, 2 mg of talc, and 1 mg of magnesium stearate were used, 5 mg of tablets prepared using twenty times larger portion of the above compounds in a mortar.

That is, 100 mg of crystals of the compound 10 were pulverized in a mortar and mixed with lactose and starch. The thus prepared formulation was mixed with 10% starch paste, and the kneaded and then subjected to granulation. After drying, the resulting granules were mixed with talc and magnesium stearate and subjected to tablet making in a usual manner.

Example 19

(5 mg of Tablets)

5 mg of tablets were obtained in a similar manner as EXAMPLE 18 by using of the compound 36.

Example 20

(20 mg of Tablets)

To give 100 mg/tablet at the ratio of which 20 mg of compound 40, 75 mg of 6% hydroxypropylcellulose/lactose, 2 mg of stearate/talc, and 3 mg of potato starch were used, 20 mg of tablets prepared using ten times larger portion of the above compounds in a mortar.

That is, 6 g of hydroxypropylcellulose was dissolved in a appropriate volume of ethanol and mixed with 94 g of lactose, followed by kneading. After drying to a degree, the mixture was passed trough a No.60 mesh, and the thus graded granules were used as 6% hydroxypropylcellulose/lactose. Separately from this, magnesium stearate and talc were mixed at ratio 1:4 and used as stearate/talc. Thereafter, the compound 40, 6% hydroxypropylcellulose/lactose, stearate/talc and potato/starch were thoroughly mixed and subjected to tablet making in a usual manner.

Example 21

(20 mg of Tablets)

20 mg of tablets were obtained in a similar manner as EXAMPLE 20 by using 200 mg of compound 36.

Example 22

(25 mg of Tablets)

To give 200 mg/tablet at the ratio of which 25 mg of compound 44, 122 mg of lactose, 50 mg of carboxymethystarch, 2 mg of talc, and 1 mg of magnesium stearate were used, 25 mg of tablets prepared using ten times larger portion of the above compounds in a mortar.

That is, 250 mg of crystals of compound 44 was pulverized in a mortar and thoroughly mixed with lactose. An appropriate volume of purified water was added to carboxymethystarch which was subsequently added to the above mixture, and the resulting mixture was kneaded and then subjected to granulation. After drying, the thus prepared granules were mixed with talc and magnesium stearate and subjected to tablet making in usual manner.

Example 23

(25 mg of Tablets)

25 mg of tablets were obtained in a similar manner as EXAMPLE 22 by using 250 mg of compound 76.

Example 24

(10 mg of Capsules)

Granules were prepared in accordance with the procedure described in EXAMPLE 16 by using 300 mg of compound 78 and packed in capsules in 100 mg portions.

Example 25

(10 mg of Capsules)

Granules were prepared in accordance with the procedure described in EXAMPLE 16 by using 300 mg of compound 10 and packed in capsules in 100 mg portions.

Example 26

(0.1% Injections)

10 mg of compound 36 (sodium salt) was dissolved in a distilled water for injection use, and total volume of the resulting solution was adjusted to 10 ml by adding a distilled water for injection use then the thus obtained solution was packed in an ampoule aseptically.

Thus, it is apparent that there has been provided, in accordance with the present invention, a treatment medicine of heart diseases which is low toxic and has excellent effects for heart diseases such as ischemic heart disease and arrhythmia and the like, and novel benzopyran derivatives useful for the thus diseases.

We claim:

1. A drug for heart disease having as an active ingredient a therapeutically effective amount of a benzopyran derivative expressed by the following

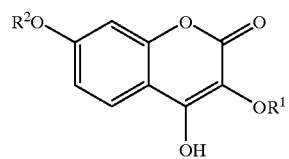
(I)

wherein $R^1$ is an alkyl group having 1–10 carbon atoms or an alkenyl group having 2–10 carbon atoms, and $R^2$ is an alkyl group having 2–4 carbon atoms and at least one hydroxyl group.

2. A benzopyran derivative expressed by the following formula (II):

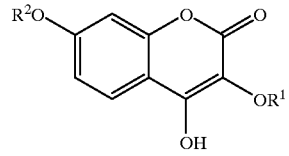

wherein $R^1$ is an alkyl group having 1–10 carbon atoms or an alkenyl group having 2–10 carbon atoms, and $R^2$ is an alkyl group having 2–4 carbon atoms and at least one hydroxyl group.

3. A method for treating heart disease comprising administering a therapeutically effective amount of a benzopyran derivative expressed by the following formula (I):

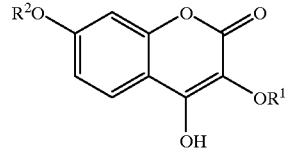

wherein $R^1$ is an alkyl group or an alkenyl group, $R^2$ is a hydrogen atom, an alkyl group, an alkyl group having a hydroxyl group, an alkenyl group, an acyl group or a glycosyl group; or physiologically acceptable salts thereof.

4. A method for treating heart disease in accordance with claim 3, wherein $R^1$ is an alkyl group having 1–10 carbon atoms or an alkenyl group having 2–10 carbon atoms, and $R^2$ is a hydrogen atom, an alkyl group having 1–10 carbon atoms, an alkyl group having 2–4 carbon atoms and at least one hydroxyl group, an alkenyl group having 2–10 carbon atoms, an acyl group having 1–10 carbon atoms, or a glycosyl group chosen from among the group consisting of glucosyl group, mannosyl group and galactosyl group.

5. A method for treating heart disease in accordance with claim 4, wherein $R^1$ is an alkyl group having 1–10 carbon atoms.

6. A method for treating heart disease in accordance with claim 4, wherein $R^2$ is a hydrogen atom.

7. A method for treating heart disease in accordance with claim 4, wherein $R^2$ is an alkyl group having 1–10 carbon atoms, an alkyl group having 2–4 carbon atoms and at least one hydroxyl group, or an alkenyl group having 2–10 carbon atoms.

8. A method for treating heart disease in accordance with claim 4, wherein $R^2$ is an acyl group having 1–10 carbon atoms.

9. A method for treating heart disease in accordance with claim 4, wherein $R^2$ is a glycosyl group chosen from among the group consisting of glucosyl group, mannosyl group and galactosyl group.

10. A method for treating heart disease in accordance with claim 9, wherein $R^2$ is a glucosyl group.

11. A method for treating heart disease in accordance with claim 3, wherein $R^1$ is an alkyl group having 1–10 carbon atoms.

12. A method for treating heart disease in accordance with claim 11, wherein $R^2$ is a hydrogen atom.

13. A method for treating heart disease in accordance with claim 11, wherein $R^2$ is an alkyl group having 1–10 carbon atoms, an alkyl group having 2–4 carbon atoms and at least one hydroxyl group, or an alkenyl group having 2–10 carbon atoms.

14. A method for treating heart disease in accordance with claim 11, wherein $R^2$ is an acyl group having 1–10 carbon atoms.

15. A method for treating heart disease in accordance with claim 11, wherein $R^2$ is a glycosyl group chosen from among the group consisting of glucosyl group, mannosyl group and galactosyl group.

16. A method for treating heart disease in accordance with claim 15, wherein $R^2$ is a glucosyl group.

17. A method for treating heart disease in accordance with claim 3, wherein $R^2$ is a hydrogen atom.

18. A method for treating heart disease in accordance with claim 3, wherein $R^2$ is an alkyl group having 1–10 carbon atoms, an alkyl group having 2–4 carbon atoms and at least one hydroxyl group, or an alkenyl group having 2–10 carbon atoms.

19. A method for treating heart disease in accordance with claim 3, wherein $R^2$ is an acyl group having 1–10 carbon atoms.

20. A method for treating heart disease in accordance with claim 3, wherein $R^2$ is a glycosyl group chosen from among the group consisting of glucosyl group, mannosyl group and galactosyl group.

21. A method for treating heart disease in accordance with claim 20, wherein $R^2$ is a glucosyl group.

* * * * *